US012576250B1

(12) United States Patent
Hakki

(10) Patent No.: US 12,576,250 B1
(45) Date of Patent: Mar. 17, 2026

(54) APERTURED MULTILAYER BALLOON CATHETER SYSTEM

(71) Applicant: A-Hamid Hakki, Dunedin, FL (US)

(72) Inventor: A-Hamid Hakki, Dunedin, FL (US)

( * ) Notice: Subject to any disclaimer, the term of this patent is extended or adjusted under 35 U.S.C. 154(b) by 0 days.

(21) Appl. No.: 19/378,332

(22) Filed: Nov. 4, 2025

(51) Int. Cl.
*A61M 25/10* (2013.01)
*A61B 17/00* (2006.01)
*A61B 17/22* (2006.01)

(52) U.S. Cl.
CPC ....... *A61M 25/10* (2013.01); *A61B 17/22012* (2013.01); *A61B 2017/00557* (2013.01); *A61B 2017/22062* (2013.01); *A61B 2017/22065* (2013.01); *A61M 2025/1084* (2013.01); *A61M 2025/1086* (2013.01); *A61M 2205/0216* (2013.01); *A61M 2205/3331* (2013.01)

(58) Field of Classification Search
CPC .......... A61M 25/10; A61M 2025/1084; A61M 2025/1086; A61M 2205/0216; A61M 2205/3331; A61B 17/22012; A61B 2017/22062; A61B 2017/22065
See application file for complete search history.

(56) References Cited

U.S. PATENT DOCUMENTS

| | | | |
|---|---|---|---|
| 10,561,528 B2 | 2/2020 | Mazzone | |
| 2001/0031982 A1 | 10/2001 | Peterson | |
| 2002/0082592 A1 | 6/2002 | Lary | |
| 2002/0193735 A1 | 12/2002 | Stiger | |
| 2010/0042199 A1* | 2/2010 | Burton | A61M 25/104 |
| | | | 623/1.11 |
| 2018/0185192 A1 | 7/2018 | Mazzone | |
| 2023/0130458 A1 | 4/2023 | Walzman | |

* cited by examiner

*Primary Examiner* — Katherine M Shi
*Assistant Examiner* — Mohammed S Adam
(74) *Attorney, Agent, or Firm* — Larson & Larson; Frank Liebenow

(57) ABSTRACT

An apertured balloon catheter consisting of 3 segments: a proximal segment, a central segment and a distal segment. The proximal and distal segments have two layers, and the central segment has three layers. Each layer of the proximal, distal segment, and first two layers of the central segment are tethered at several points forming a space therebetween, which is selectively filled with a fluid by a conduit to expand the apertured balloon catheter. The third layer of the central segment forms a second space with the second central layer and is selectively filled by a separate conduit to expand against the vessel wall. The proximal balloon segment and the distal balloon segment have apertures within the tether points that communicate with the lumen of the blood vessel within the inflated balloon chamber. The size of the apertures is set to capture blood debris flowing through the apertured balloon catheter.

20 Claims, 3 Drawing Sheets

APERTURED MULTILAYER BALLOON CATHETER SYSTEM

FIELD OF THE INVENTION

This invention relates to the field of medicine, and in particular to surgical devices inserted into a patient's vascular system that, for example, dilate blocked arteries, open narrowed valves, deliver medications, ultrasound, laser, and/or pacemaker therapy directly to the tissues.

BACKGROUND OF THE INVENTION

Balloon catheters have been used for intravascular applications for many years to dilate blockages, perform ultrasound or laser lithotripsy, and to control vascular dissections. On Jan. 16, 1964 Dotter and Judkins performed the first balloon angioplasty of a lower extremity. On Sep. 16, 1977, Andreas Gruntzig performed the first balloon coronary angioplasty. Such balloon technology often blocked blood flow through the blood vessel in which they are inserted.

When the balloon catheters of the prior art are inflated, blood flow is interrupted and prolonged inflation may cause complications due to decreased blood flow resulting in tissue ischemia or necrosis. Previously, auto perfusion balloon catheters provided minimal blood flow through a central lumen and multiple side holes in the proximal and distal shafts but have not been very effective and are no longer in clinical use.

Prior art catheters to capture debris and blood clots such as during aortic valve procedures have not been very effective in preventing cerebrovascular events.

Prior balloon catheters had layers made of thermoplastic polymers such as nylons, polyurethanes, polyolefins, PET (polyethylene terephthalate) and Pebax that provide strength, flexibility and ability to stretch and recoil under pressure.

What is needed is a mechanism that provides balloon inflation that is needed for a specific purpose such as angioplasty, valvuloplasty, transcatheter aortic valve replacement (TAVR), aortic dissection, occluded vessel, coronary stenosis, vascular lithotripsy or laser therapy without compromising blood flow through the vessel. It would also be ideal to provide a mechanism to collect blood clots and debris preventing them from going downstream during vascular procedures. For nonvascular applications such as gastrointestinal, esophageal, urethral, ureteral, prostate, as well as other applications that require maintaining of flow of biological fluids while the balloon is inflated, or air flow as in respiratory bronchial applications.

SUMMARY OF THE INVENTION

In one embodiment, an apertured balloon catheter is disclosed including an internal conduit extending in a longitudinal direction having a catheter lumen for accepting a guide wire. A balloon is coupled to the internal conduit and the balloon has layers that include an inner balloon layer and an outer balloon layer forming therein a first space therebetween. A first conduit extends within the balloon and is in fluid communication with the first space for selectively filling the first space with a fluid. There are several tethers connecting the inner balloon layer and the outer balloon layer. Each tether has an orifice for passing of a body fluid from outside of the apertured balloon catheter to inside of the apertured balloon catheter and from inside of the apertured balloon catheter to outside of the apertured balloon catheter, thereby permitting flow of the body fluid through the apertured balloon catheter.

In another embodiment, an apertured balloon catheter for delivering therapy within a body-tube is disclosed. The apertured balloon catheter includes an internal conduit that has a hollow core for accepting a guide wire. A longitudinal body has a proximal segment affixed to one end of the internal conduit and has a first proximal layer and a second proximal layer. A distal segment is affixed to a distal second end of the internal conduit and has a first distal layer and a second distal layer. A central segment is affixed at one end to the proximal segment and at a second distal end to the distal segment. The central segment has a first central layer, a second central layer, and a third central layer. A proximal space is formed between the first proximal layer and the second proximal layer, a distal space is formed between the first distal layer and the second distal layer, a central space is formed between the first central layer and the second central layer, and a second central space is formed between the second central layer and the third central layer. A first conduit is fluidly interfaced to the proximal space, to the distal space, and to the central space for delivering a fluid for inflation and a second conduit is fluidly interfaced to the second central space for delivering the fluid for inflation. A first set of apertures are formed between the first proximal layer and the second proximal layer; and a second set of apertures are formed between the first distal layer and the second distal layer.

In another embodiment, a method for delivering therapy within a body-tube is disclosed including providing an apertured balloon catheter that includes an internal conduit that has a hollow core for accepting a guide wire. The apertured balloon catheter includes a longitudinal body having a proximal segment affixed to one end of the internal conduit and a first proximal layer and a second proximal layer, a distal segment affixed to a distal second end of the internal conduit that has a first distal layer and a second distal layer, a central segment affixed at one end to the proximal segment and at a second distal end to the distal segment. The central segment has a first central layer, a second central layer, and a third central layer. There is a proximal space between the first proximal layer and the second proximal layer and a distal space between the first distal layer and the second distal layer. There is a central space between the first central layer and the second central layer and a second central space between the second central layer and the third central layer. A first conduit is fluidly interfaced to the proximal space, to the distal space, and to the central space for delivering a fluid for inflation. A second conduit is fluidly interfaced to the second central space for delivering the fluid for inflation. A first set of apertures are formed between the first proximal layer and the second proximal layer and a second set of apertures are formed between the first distal layer and the second distal layer. The method includes positioning a guide wire in a body-tube and threading an end of the guide wire through the hollow core of the apertured balloon catheter. Next, the apertured balloon catheter is guided into the body-tube along the guide wire, pushing the apertured balloon catheter through the body-tube until the apertured balloon catheter is positioned at a desired location then injecting the fluid under pressure into the first conduit and into the second conduit, thereby the apertured balloon catheter expands within the body-tube such that the apertured balloon catheter at least touches inner walls of the body-tube or applies force against the inner walls of the body-tube, thereby expanding the body-tube.

In another embodiment, a medical device includes an elongated body or shaft. A balloon is located at the distal part of the elongated body and is composed of two or more layers, the layers are tethered (such as biologically compatible adhesive, by heat, thermal fusing or laser) at several points, in the center of the tethered layers are optionally placed holes or apertures, and in some embodiments, one or more ultrasound emitters are longitudinally located along the central balloon layers. The ultrasound emitters propagate high energy pressure waves directly to the vessel endothelium and calcified plaques in the vessel wall. The balloon layers are configured to receive fluid to expand the balloon layers(s) by creating an enclosed space open only to the outside of the patient's body, and inflate so that the exterior surface of the balloon abuts against the inner lining of the vessel wall, while creating a lumen around the elongated body or shaft that fills with flowing blood maintaining blood flow through the vessel. The elongated body or shaft and wire are configured to navigate through tortuous vessel course to the destination of the vessel blockage and calcium buildup. In some embodiments, radio opaque indicators are located along the elongated body or balloon surface for proper positioning of the balloon within the vessel wall. The apertured multilayer balloon catheter comprises a proximal balloon segment, a central balloon segment, and a distal balloon segment. The proximal balloon segment has a first set of apertures within the tethered points, and the distal balloon segment has a second set of apertures within the tethered points. The attachment points between the first and second balloon layers are either closed without openings or holes (central balloon segment) or apertures (proximal and distal balloon segments). Apertures or holes in the balloon layers are limited to the proximal balloon segment and the distal balloon segment so that blood flows through the apertures into the lumen created by the inflated balloon around the elongated body (shaft) of the catheter and out the distal apertures of the distal balloon segment. The balloon is comprised of two or more layers that are tethered to each other at several points creating a closed space(s) between them that is collapsed around the elongated body (shaft) catheter for introduction into the vascular system, and the layers expand when filled with fluid via one or more conduits embedded in the elongated body or shaft catheter wall extending to the outside of the patient.

In another embodiment, a system for delivering therapy within a blood vessel is disclosed, including an apertured multilayer balloon catheter that includes a proximal balloon segment, a central balloon segment, and a distal balloon segment. The proximal balloon segment has a first set of apertures, and the distal balloon segment has a second set of apertures. The layers of the balloon are tethered using biologically compatible adhesive, heating probe or laser. The heating probe or laser has the advantage of not only tethering two layers but at the same time creating an aperture in the center of the adhered layers. The catheter longitudinal body has an internal conduit for accepting a guide wire. The guide wire is positioned in a vessel, and an end of the guide wire is threaded through the internal conduit of the longitudinal body catheter such that the balloon catheter is guided into the body vessel by the guide wire. The apertured balloon catheter is pushed through the vascular system until the apertured balloon catheter reaches a location for delivering the therapy, such as dilatating a blocked artery and then, fluid under pressure is injected into space between the two (or more) layers, thereby the apertured balloon catheter expands the balloon cavity within the vessel such that the apertured balloon catheter either touches inner walls of the vessel or expands further to stretch the vessel wall.

In another embodiment, a method for delivering therapy within a vessel is disclosed. The method includes positioning a guide wire in a blood vessel and threading an end of the guide wire through an internal conduit of the apertured balloon catheter. The apertured balloon catheter has a body with a proximal balloon segment, a central balloon segment, and a distal balloon segment. The proximal balloon segment has a first set of apertures, and the distal balloon segment has a second set of apertures. The method continues with pushing the apertured balloon catheter through the vessel until the apertured balloon catheter reaches a location for delivering the therapy and then providing fluid under pressure into the enclosed space(s) between the balloon layers, thereby expanding the apertured balloon catheter within the vessel such that the apertured balloon catheter either touches inner walls of the vessel or expands to stretch the vessel wall.

In some embodiments, the apertured balloon catheter system is directed to surgical devices inserted into a patient's vascular system for expanding blockages, opening valvular stenoses, delivering medications, ultrasound, laser, and pacemaker therapy directly to the tissues.

In some embodiments, the apertured balloon catheter system is directed to balloon catheter systems which are inserted into a patient's vascular system and remain in a relatively fixed location during or after a medical procedure.

In some embodiments, the apertured balloon catheter system is directed to a balloon catheter system which includes a balloon construction which allows for retention and simultaneous application of therapeutic interventions while maintaining blood flow proximal and distal to the balloon.

In some embodiments, the apertured balloon catheter system is directed to a balloon catheter system which includes one or more layers that is/are filled with liquid under pressure to cause deployment (expansion) of the balloon layers against the inner lining of the vascular system or valvular structures.

In some embodiments, the apertured balloon catheter system is directed to a balloon catheter system having a one or more balloon orifices formed through the proximal as well as distal segments of the balloon.

In some embodiments, the apertured balloon catheter system is directed to a balloon catheter system which has a mechanism for providing medicants to be inserted through the enclosed spaces within the balloon for treating a particular ailment.

In some embodiments, the apertured balloon catheter system is directed to an open balloon catheter system which is inserted into the vascular system of a patient for restraining the balloon catheter from movement while simultaneously providing therapeutic interventions with angioplasty, stent placement, ultrasound, laser, pacemaker therapy and medications.

In some embodiments, the apertured balloon catheter system is directed to a balloon catheter is placed in a diseased heart valve such as aortic stenosis to expand the aortic valve orifice without disrupting blood flow through the valve by way of apertures in the proximal and distal parts of the balloon.

In some embodiments, the apertured balloon catheter system is directed to a balloon that is placed at the site of vascular tear or dissection, such as the aorta to stop bleeding while maintaining blood flow to the distal aorta and downstream tissues.

In some embodiments, during a cardiac valve replacement such as TAVR (transcatheter aortic valve replacement), the apertured balloon catheter is placed distal to the aortic valve to capture debris or clots that result from manipulations of the diseased heart valve.

In some embodiments, the apertured balloon catheter is placed to disrupt vascular plaque (angioplasty) and improve blood flow through the diseased coronary artery.

In some embodiments, the apertured balloon catheter has a third balloon exterior to the second ballon layer and is limited to the central balloon segment that is inflated by a separate conduit to provide more effective vessel dilatation and disruption of vascular plaque (angioplasty) and improve blood flow through the diseased coronary artery.

In some embodiments, the apertured balloon catheter provides pacing cardiac tissue in the event of profound bradycardia or heart block.

In some embodiments, the apertured balloon catheter provides for smaller orifice dimensions in the proximal balloon segment to capture unwanted blood clots, plaque and other debris entering the balloon segment from the larger orifices of the distal segment, while maintaining blood flow.

In some embodiments, the apertured balloon catheter provides for larger orifice dimensions in the proximal balloon segment to capture unwanted blood clots, plaque and other debris from exiting the balloon segment from the smaller orifices of the distal segment, while maintaining blood flow.

In some embodiments, balloon layers are made of elastic material that return to their original shapes and sizes after being deflated.

In another embodiment one or more balloon layers are made of materials that are semi-elastic such as the material exhibits both elastic and inelastic properties.

In yet another embodiment, one or more balloon layers are made of inelastic material.

BRIEF DESCRIPTION OF DRAWINGS

The invention can be best understood by those having ordinary skill in the art by reference to the following detailed description when considered in conjunction with the accompanying drawings in which.

DETAILED DESCRIPTION OF THE INVENTION

Figure 1:
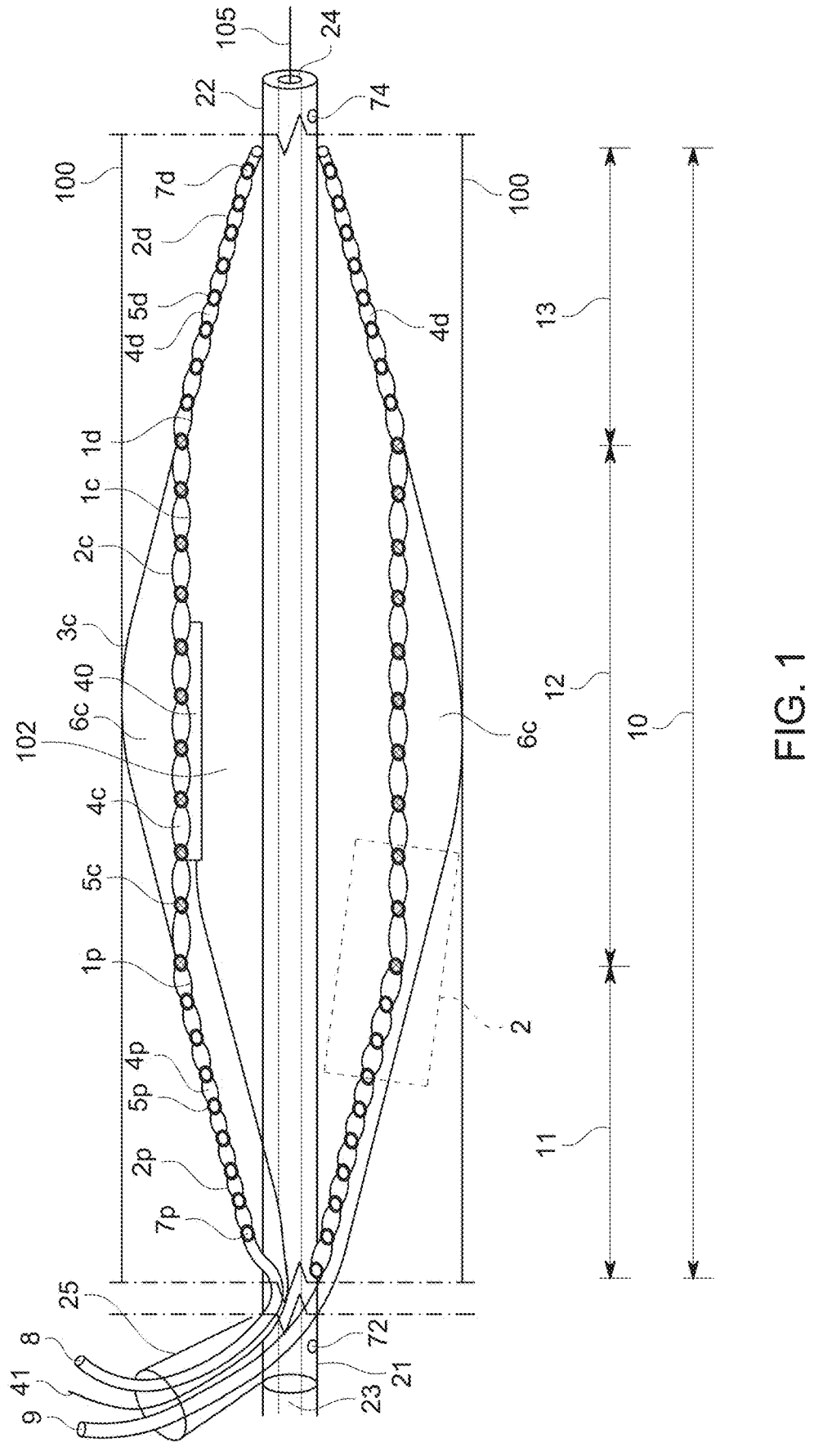
FIG. 1 is a is a schematic view of the apertured balloon catheter system shown in an expanded configuration with 2-layered balloon filled with fluid by way of a separate conduit attached to each other at several locations in the proximal balloon segment, central balloon segment and the distal balloon segment. A $3^{rd}$ balloon layer overlaps the central balloon segment, filled by a second conduit and having an optional, longitudinally placed, ultrasonic emitter.

Reference will now be made in detail to the presently preferred embodiments of the invention, examples of which are illustrated in the accompanying drawings. Throughout the following detailed description, the same reference numerals refer to the same elements in all figures.

Throughout this description, the term "balloon" or "apertured balloon" refer to a device that is positioned in the distal portion of in a tube, for example using a catheter, and inflated to expand within the tube for any known reason such as holding the apertured balloon in place or increasing the diameter of a blood vessel. The apertured balloon has features that allow a fluid (e.g., blood) to flow through such that the apertured balloon does not significantly block such flow. In some embodiments, the apertured balloon provides medications directly to an area of the tube in which it is placed (e.g., chemotherapy). In some embodiments, the apertured balloon carries other medical devices such as ultrasonic emitters (e.g., for removing calcified coronary plaques or dissolving kidney stones), lasers, etc.

In some embodiments, the fluid contains therapeutic agents delivered in close proximity to the lining of the vessel 100 in which the apertured balloon catheter 10 is inserted. In some embodiments, the fluid is heated/cooled to provide a desired temperature to the surface of the apertured balloon catheter 10, thereby heating or cooling the lining of the vessel 100 in which the apertured balloon catheter 10 is inserted. This is often the case when performing procedures in arteries such as for stenting or ultrasound lithotripsy. In such, when concerned with particulate matter (e.g., blood clots or debris), the smaller apertures 7p are at the proximal end to capture the particulate matter within the apertured balloon catheter 10.

Note that, as the apertured balloon catheter 10 is typically inserted through an access into a vessel 100, the distal balloon segment 13 of the apertured balloon catheter 10 is inserted first (e.g., furthest from the access) and the proximal balloon segment 11 is that which is closest to the access point. In some usage scenarios, body fluid (e.g., blood) flows from the distal end towards the proximal end such that as the apertured balloon catheter 10 is being inserted, it is inserted against the flow of fluid (e.g., blood).

Figure 2:
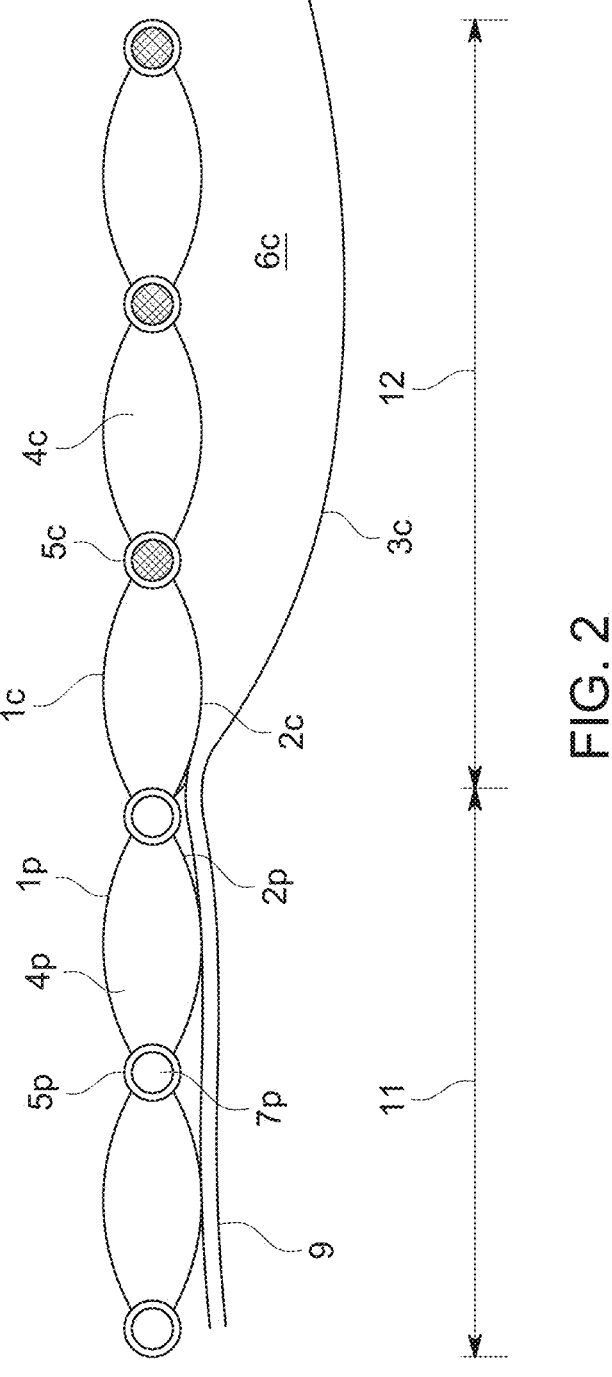
FIG. 2 is a schematic view of the apertured balloon catheter system shown in an Inflated configuration with two layers in the proximal balloon segment attached to the central balloon segment.

Referring to FIG. 1 and FIG. 2, the apertured balloon catheter 10 is shown. The proximal balloon segment 11 has two layers, inner proximal layer 1p and outer proximal layer 2p. Enclosed between the inner proximal layer 1p and the outer proximal layer 2p is a proximal space 4p that is selectively filled with a fluid flowing from the conduit 8 (a liquid such as saline solution or a gas such as nitrogen is provided when the balloon is being deployed and ready for expansion). The central balloon segment 12 has three layers, inner central layer 1c, middle central layer 2c and outer central layer 3c. The conduit 8 is in fluid communications with the central space 4c between the inner central layer 1c and the middle central layer 2c. A second conduit 9 is in fluid communications with a second central space 6c formed between the outer central layer 3c and the middle central layer 2c. When deployed such as for angioplasty or valvuloplasty, the second conduit 9 provides fluid pressure to the second central space 6c. The distal balloon segment has two layers: inner distal layer 1d and outer distal layer 2d in fluid communications with the conduit 8.

The proximal balloon segment 11 has proximal tethered points 5p with proximal apertures 7p in their center to allow fluid (e.g., blood) to flow into or out of space 102.

The distal balloon segment 13 has distal tether points 5d with distal apertures 7d in their center to allow fluid (e.g., blood) to flow into or out of the space 102.

The center balloon segments 12 has central tethers 5c but does not have apertures.

Each of tether points (proximal tether point 5p, distal tether points 5d, central tether points 5c) are the attachment points between the inner layers (inner proximal layer 1p, inner distal layer 1d, inner central layer 1c) and the outer layers (outer proximal layer 2p, outer distal layer 2d and outer central layer 2c). In some embodiments, they are made using a biologically compatible adhesive, or a laser beam or a heated probe that attach the inner layers 1p/1c/1d to the outer layers 2p/2c/2d at certain points along the entire apertured balloon catheter 10, and at the same time creating the proximal apertures 7p or distal apertures 7d (e.g., apertures or holes) in the center of the attachment points. To inflate the apertured balloon catheter 10 and fill the space 102 (e.g., the space 102 is filled with blood), the proximal space 4p, central space 4c, and distal space 4d, between the inner layers 1p/1c/1d to the outer layers 2p/2d or middle central layer 2c is filled with a fluid (e.g., saline or nitrogen gas) typically from outside the body using conduit 8. The second conduit 9 is used to fill the second central space 6c between the middle central layer 2c and outer central layer 3c with the fluid (e.g., saline or nitrogen gas).

In some embodiments, the proximal apertures 7p and distal apertures 7d are sized to capture debris and clots that enter the apertured balloon catheter 10. For example, when proximal apertures 7p are larger than the distal apertures 7d, when such debris and/or clots flow into the apertured balloon catheter 10 through the proximal apertures 7p, the debris and/or clots are captured within the apertured balloon catheter 10 when the debris and/or clots are larger than the distal apertures 7d.

The conduit 8 is fluidly interfaced to the proximal space 4p, the central space 4c and the distal space 4d created between the inner proximal layer 1p and the outer proximal layer 2p, the inner central layer 1c and the middle central layer 2c and the inner distal layer 1d and outer distal layer 2d which are spaces that are in fluid communications with each other and when filled with fluid, such spaces expand to create a space 102 that, during use, will be filled with and allow the flow of body fluid (e.g., blood) surrounding elongated body shaft 21/22. For simplicity, proximal apertures 7p are typically holes in the proximal balloon segment 11 and distal apertures 7d are holes in the distal balloon segment 13. There are no apertures or holes within tethered points 5c between, the inner central layer 1c and the middle central layer 2c of the central balloon segment 12. The proximal tether points 5p are the points of adherence of the inner proximal layer 1p and the outer proximal layer 2p surrounding aperture 7p and distal tether points 5d are the points of adherence of inner distal layer 1d and outer distal layer 2d surrounding the respective distal apertures 7d.

Three sections of the apertured balloon catheter 10 include a proximal ballon segment 11, a central balloon segment 12 and a distal balloon segment 13. In some embodiments, the proximal balloon segment 11 and the distal balloon segment 13 are generally cone shaped, and the central balloon segment 12 is generally cylindrical. The proximal apertures 7p and distal apertures 7d are openings in the proximal balloon segment 11 and distal balloon segment 13, respectively, enabling fluids within the vessel 100 (e.g., blood) to flow through the proximal balloon segment 11, central balloon segment 12, and distal balloon segment 13, especially while the apertured balloon catheter 10 is inflated as shown in FIG. 1.

The conduit 8 and second conduit 9 typically run distal from the apertured balloon catheter 10 through the vessel 100 and outside of the patient while the apertured balloon catheter 10 is within the patient. Therefore, the conduit 8 and second conduit 9 are contained within a bundle 25 that optionally contains any wires 41 or other conductors of power or sensor data (e.g., sensors 72/74 which are anticipated to be any sensors such as pressure sensors, cameras, etc.). In the embodiment shown, the wire(s) 41 are connected to an ultrasonic emitter 40.

The apertured balloon catheter 10 is typically guided through the vessel 100 by a guide wire 105 that passes through an internal conduit 23/24 from the proximal end 21 to the distal end 22.

In embodiments that have one or more proximal sensors 72 and/or distal sensors 74, it is anticipated that pressure and blood flow within the apertured balloon catheter 10 be measured to determine the loss of blood flow caused by the inflated apertured balloon catheter 10, especially as particulate material is captured within the apertured balloon catheter 10 (e.g., particulate material such as blood clots and debris that are small enough to enter the apertured balloon catheter 10 through distal apertures 7d yet such particulate matter is too large to pass through proximal apertures 7p that are smaller). Again, as stated above, for body fluid flow in the opposite direction, the proximal apertures 7p are larger than the distal apertures 7d.

Fluid pressure is typically provided by pumps and monitored by sensors that are outside the patient connected to the apertured balloon catheter 10 conduit 8 and second conduit 9. It is anticipated that the fluid pressure be adjusted to keep the apertured balloon catheter 10 inflated and, in cases of vascular dissections, to keep pressure against the vessel at a level needed to control bleeding. In some embodiments, blood pressure and blood flow are measured by proximal sensors 72 and distal sensors 74.

Although any flow of a fluid (e.g., blood, bile, urine, air) within the body-tube or vessel 100 is anticipated, in some usage scenarios, the fluid flows from the distal end of the apertured balloon catheter 10 towards the proximal end of the apertured balloon catheter 10, though the opposite is fully anticipated.

In some embodiments, the distal apertures 7d and proximal apertures 7p are large enough for anticipated particulate matter (e.g., blood clot or debris) to enter into the apertured balloon catheter 10, pass through the apertured balloon catheter 10, and exit out of the proximal apertures 7p while allowing flow of a fluid (e.g., blood) through the vessel 100 in which the apertured balloon catheter 10 is inserted. In some embodiments, the distal balloon apertures 7d are made to be smaller, thereby blocking any anticipated particulate matter (e.g., blood clot or debris) from entering the apertured balloon catheter 10 while allowing flow of a fluid (e.g., blood) through the vessel 100 in which the apertured balloon catheter 10 is inserted.

As shown in FIG. 1, in some embodiments, the distal apertures 7d are large enough for anticipated particulate matter (e.g., blood clot or debris) to enter into the apertured balloon catheter 10, but the proximal apertures 7p are smaller than the distal apertures 7d, allowing flow of a fluid (e.g., blood) but capturing the particulate matter (e.g., blood clots or debris) that is smaller than the distal apertures 7d, yet larger than the proximal apertures 7p. Such particulate matter is captured within the apertured balloon catheter 10.

Although it is anticipated that the proximal apertures 7p and the distal apertures 7d of the apertured balloon catheter 10 be of any shape (e.g., round, oval, triangular, rectangular), for brevity and clarity reasons, the proximal apertures 7p and the distal apertures 7d are shown as being round. When the distal apertures 7d at the distal end of the apertured balloon catheter 10 are round, the distal apertures 7d at the distal end of the apertured balloon catheter 10 have a first total area (e.g., sum of $\Pi r^2$ of each distal aperture 7d). When the proximal apertures 7p at the proximal end of the apertured balloon catheter 10 are round, the proximal apertures 7p at the proximal end of the apertured balloon catheter 10 have a second total area (e.g., sum of $\Pi r^2$ of each aperture).

As in some embodiments of the apertured balloon catheter 10, the proximal balloon segment 11 and distal balloon segment 13 are generally cone-shaped, the length (l) of each of the proximal balloon segment 11 and distal balloon segment 13 with respect to the radius (r) of each where the proximal balloon segment 11 and distal balloon segment 13 meet the center segment 12 of the apertured balloon catheter 10 define an area of each of the proximal balloon segment 11 and distal balloon segment 13. Therefore, the surface area of each proximal balloon segment 11 and distal balloon segment 13 is approximately this $\Pi r l$. In embodiments in which the length (l) is approximately twice the radius (r), to reduce or eliminate reduction of fluid flow through the apertured balloon catheter 10 after insertion and inflation, it is anticipated that the first area be a minimum of 50% of the surface area of the distal balloon segment 13 and that the second area be a minimum of 50% of the surface area of the proximal balloon segment 11. It is fully anticipated that the first area and second area be greater than 50% of the surface area of the respective proximal segment 11 or distal segment 13 so long as the structure of the distal segment 13 and proximal segment 11 are maintained. (e.g., as the area of the proximal apertures 7p and the distal apertures 7d approach the area of the respective proximal balloon segment 11 and distal balloon segment 13, then there is very little material devoted to the proximal balloon segment 11 and distal balloon segment 13, thereby reducing structural strength of each of the proximal balloon segment 11 and distal balloon segment 13. Therefore, if increased flow-thru is needed, the length (l) is increased to allow for greater total area of the proximal apertures 7p and the distal apertures 7d. It is also anticipated that the first area and/or the second area be less than 50% of the surface area of the respective proximal segment 11 or distal segment 13, understanding that there will be some limitations to fluid flow through this embodiment of the apertured balloon catheter 10.

In some embodiments, the length (l) is four times the radius (r) and in such, to reduce or eliminate reduction of fluid flow through the apertured balloon catheter 10 after insertion and inflation, it is anticipated that the first area be a minimum of 25% of the surface area of the distal segment 13 and that the second area be a minimum of 25% of the surface area of the proximal balloon segment 11. As above, it is fully anticipated that the first area and second area be greater than 25% of the surface area of the respective segment 11/13 so long as the structure of the distal balloon segment 13 and proximal balloon segment 11 are maintained. (e.g., as the area of the proximal apertures 7p and distal apertures 7d approach the area of the respective proximal balloon segment 11 and distal balloon segment 13, then there is very little material devoted to the proximal balloon segment 11 and distal balloon segment 13, thereby reducing structural strength of each of the proximal balloon segment 11 and distal balloon segment 13). Therefore, if increased flow-thru is needed, the length (l) is increased to allow for greater area totals for the proximal apertures 7p and the distal apertures 7d. It is also anticipated that the first area and/or the second area be less than 25% of the surface area of the respective proximal segment 11 and distal segment 13, understanding that there will be some limitations to fluid flow through this embodiment of the apertured balloon catheter 10.

Referring to FIG. 2, an expanded view of one side of the proximal segment 11 and central segment 12 is shown. In this, it is shown that the central tethers 5c are typically closed, though in some embodiments, they are open, but not connected to any conduit.

Figure 3A:
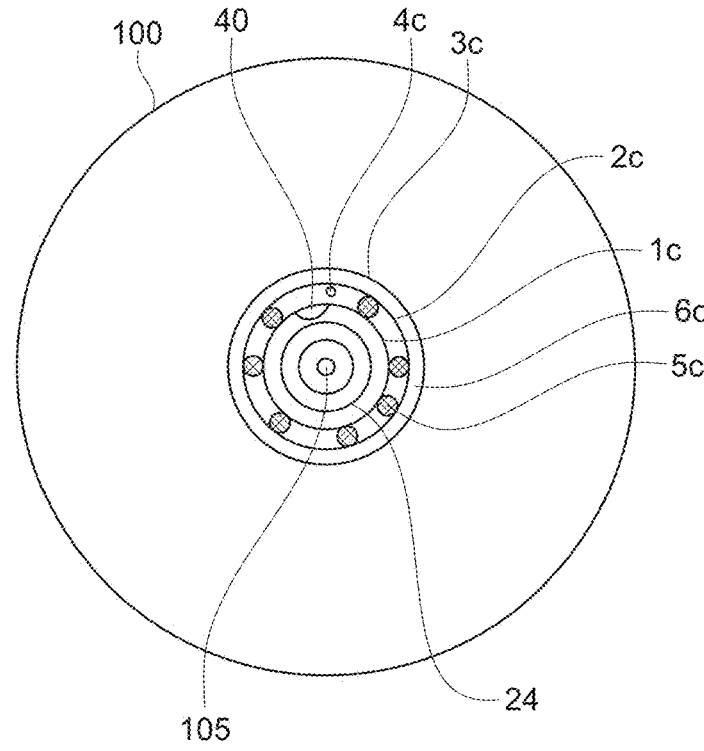
FIG. 3A is a view of the three layers of the balloon in a collapsed configuration around the central longitudinal catheter body or shaft such as by balloon material that is elastic.

Referring to FIG. 3A, the three layers of the apertured balloon catheter 10 are shown collapsed around the central longitudinal catheter body 24 or shaft.

Figure 3B:
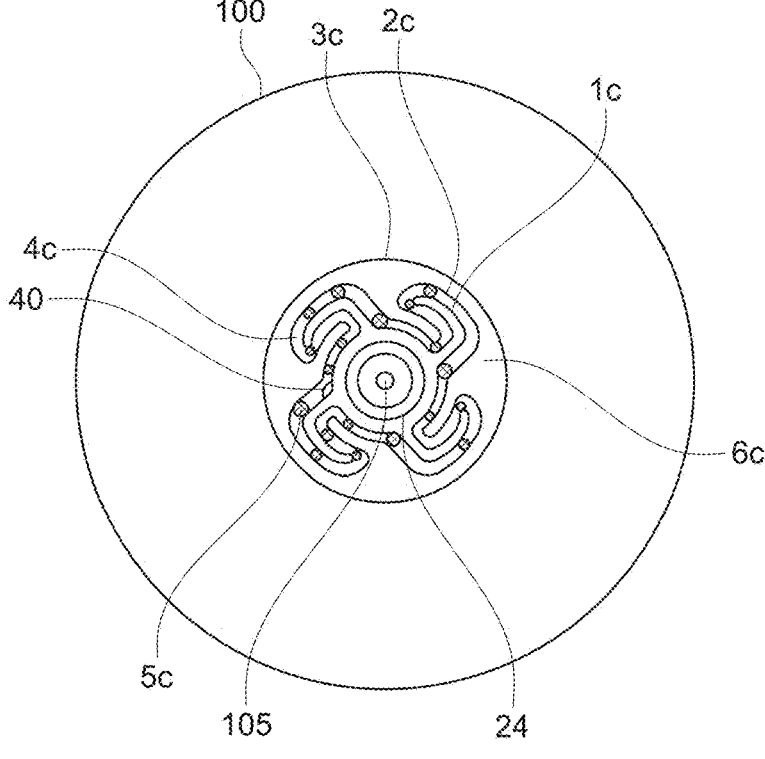
FIG. 3B is a view of the first and second balloon layers folded/collapsed around the central longitudinal catheter body or shaft, covered by the collapsed third balloon layer.

Referring to FIG. 3B, the first and second balloon layers are shown folded/collapsed around the central longitudinal catheter body 24 or shaft, covered by the collapsed third balloon layer. In some embodiments, the third layer is made from any know material such as balloon materials that are semi-elastic and inelastic.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. An apertured balloon catheter comprising:
   a internal conduit extending in a longitudinal direction having a catheter lumen for accepting a guide wire;
   a balloon coupled to the internal conduit, the balloon having layers comprising an inner balloon layer and an outer balloon layer forming therein a first space therebetween;
   a first conduit extending within said balloon, the first conduit in fluid communication with the first space for selectively filling the first space with a fluid, and
   a plurality of tethers connecting the inner balloon layer and the outer balloon layer, each tether of the plurality of tethers having an orifice for passing of a body fluid from outside of the apertured balloon catheter to inside of the apertured balloon catheter and from inside of the apertured balloon catheter to outside of the apertured balloon catheter, thereby permitting flow of the body fluid through the apertured balloon catheter.

2. The apertured balloon catheter of claim 1, further comprising a third balloon layer, a first end of the third balloon layer connected to the outer balloon layer at a point in which a central balloon segment meets a distal balloon segment and a distal second end of the third balloon layer connected to the outer balloon layer at a second point in which the central balloon segment meets a proximal balloon segment defining a second space between the third balloon layer and the outer balloon layer; a second conduit extending within said balloon, the second conduit in fluid communication with the second space for selectively filling the second space with the fluid.

3. The apertured balloon catheter of claim 2, further comprising a sensor interfaced to the proximal balloon segment or the distal balloon segment.

4. The apertured balloon catheter of claim 2, further comprising an ultrasonic emitter device affixed to the central balloon segment.

5. The apertured balloon catheter of claim 1, wherein said inner balloon layer and said outer balloon layer are formed of a material that is substantially flexible and inelastic.

6. The apertured balloon catheter of claim 5, wherein said third balloon layer is formed of a second material that is substantially flexible and more elastic than the material.

7. The apertured balloon catheter of claim 1, wherein said inner balloon layer is tethered to said outer balloon layer by a plurality of tether members.

8. The apertured balloon catheter of claim 7, wherein each tether of the plurality of tether members are spaced substantially equidistant from each other and said plurality of tether members are flexible and substantially inelastic.

9. The apertured balloon catheter of claim 7, wherein each tether of the plurality of tether members are selected from a group consisting of thread elements and band elements for structurally maintaining a substantially equal distance from said inner balloon layer and said outer balloon layer when the fluid is forced into said first conduit.

10. The apertured balloon catheter of claim 7, wherein each tether of the plurality of tether members comprise a set of proximal tether members, a set of distal tether members and a set of central tether members.

11. The apertured balloon catheter of claim 10, wherein the set of proximal tether members and the set of distal tether members each have the orifice for passing of the body fluid from outside of the apertured balloon catheter to inside of the apertured balloon catheter and from inside of the apertured balloon catheter to outside of the apertured balloon catheter, thereby permitting flow of the body fluid through the apertured balloon catheter.

12. The apertured balloon catheter of claim 11, wherein each tether in the set of proximal tether members have larger orifices than each tether in the set of distal tether members for capturing debris and/or blood clots in the set of distal tether members.

13. The apertured balloon catheter of claim 11, wherein each tether in the set of distal tether members have larger orifices than each tether in the set of proximal tether members for capturing debris and/or blood clots in the set of proximal tether members.

14. An apertured balloon catheter for delivering therapy within a body-tube, the apertured balloon catheter comprising:

an internal conduit that has a hollow core for accepting a guide wire;

a longitudinal body having a proximal segment affixed to one end of the internal conduit and having a first proximal layer and a second proximal layer, a distal segment affixed to a distal second end of the internal conduit and having a first distal layer and a second distal layer, a central segment affixed at one end to the proximal segment and at a second distal end to the distal segment, the central segment having a first central layer, a second central layer, and a third central layer; a proximal space is between the first proximal layer and the second proximal layer, a distal space is between the first distal layer and the second distal layer, a central space is between the first central layer and the second central layer, a second central space is between the second central layer and the third central layer;

a first conduit is fluidly interfaced to the proximal space, to the distal space, and to the central space for delivering a fluid for inflation;

a second conduit is fluidly interfaced to the second central space for delivering the fluid for the inflation;

a first set of apertures are formed between the first proximal layer and the second proximal layer; and a second set of apertures are formed between the first distal layer and the second distal layer.

15. The apertured balloon catheter of claim 14, wherein after the fluid under pressure is injected into the distal space, the central space, the second central space and the proximal space, body fluid will flow into the first set of apertures, through a central balloon segment and out of the second set of apertures.

16. The apertured balloon catheter of claim 15, wherein the first set of apertures have a first cross-sectional area and the second set of apertures have a second cross-sectional area and the first cross-sectional area is greater than the second cross-sectional area such that debris entering the first set of apertures is captured within the apertured balloon catheter.

17. A method for delivering therapy within a body-tube, the method comprising:

providing an apertured balloon catheter comprising:

an internal conduit that has a hollow core for accepting a guide wire;

a longitudinal body having a proximal segment affixed to one end of the internal conduit and having a first proximal layer and a second proximal layer, a distal segment affixed to a distal second end of the internal conduit and having a first distal layer and a second distal layer, a central segment affixed at one end to the proximal segment and at a second distal end to the distal segment, the central segment having a first central layer, a second central layer, and a third central layer; a proximal space is between the first proximal layer and the second proximal layer, a distal space is between the first distal layer and the second distal layer, a central space is between the first central layer and the second central layer, a second central space is between the second central layer and the third central layer;

a first conduit is fluidly interfaced to the proximal space, to the distal space, and to the central space for delivering a fluid for inflation;

a second conduit is fluidly interfaced to the second central space for delivering the fluid for inflation;

a first set of apertures are formed between the first proximal layer and the second proximal layer; and a second set of apertures are formed between the first distal layer and the second distal layer;

positioning a guide wire in a body-tube;

threading an end of the guide wire through the hollow core of the apertured balloon catheter;

guiding the apertured balloon catheter into the body-tube along the guide wire;

pushing the apertured balloon catheter through the body-tube until the apertured balloon catheter is positioned at a desired location; and injecting the fluid under pressure into the first conduit and into the second conduit, thereby the apertured balloon catheter expands within the body-tube such that the apertured balloon catheter at least touches inner walls of the body-tube or applies force against the inner walls of the body-tube, thereby expanding the body-tube.

18. The method for delivering the therapy within the body-tube of claim 17, wherein the body-tube is a blood vessel.

19. The method for delivering the therapy within the body-tube of claim 18, wherein after injecting the fluid under pressure into the first conduit and into the second conduit and, therefore, into the distal space, the central space, the second central space and the proximal space, a body-fluid flows into the first set of apertures, through the central segment and out of the second set of apertures.

20. The method for delivering the therapy within the body-tube of claim 19, wherein the first set of apertures have a first cross-sectional area and the second set of apertures have a second cross-sectional area and the first cross-sectional area is greater than the second cross-sectional area, therefore, capturing debris that enters the first set of apertures within the apertured balloon catheter.

\* \* \* \* \*